United States Patent [19]
Cody et al.

[11] Patent Number: 5,974,887
[45] Date of Patent: Nov. 2, 1999

[54] METHOD FOR DETERMINING OPERATING STATUS OF LIQUID PHASE GAS-PHASE INTERACTION COLUMNS

[75] Inventors: George Dewey Cody, Princeton, N.J.; David R. Johnsrud, Baton Rouge, La.; Uri Sela, Walnut Creek, Calif.

[73] Assignee: Exxon Research and Engineering Co., Florham Park, N.J.

[21] Appl. No.: 08/938,348

[22] Filed: Sep. 26, 1997

[51] Int. Cl.$^6$ .................................................... G01N 9/24
[52] U.S. Cl. .............................. 73/602; 73/579; 73/19.01
[58] Field of Search .............................. 73/579, 602, 609, 73/610, 613, 861.18, 861.21, 19.01, 19.03, 19.1; 201/1; 702/54, 56

[56] References Cited

U.S. PATENT DOCUMENTS

| | | |
|---|---|---|
| 3,012,848 | 12/1961 | Levey et al. ............................. 23/14.5 |
| 3,553,636 | 1/1971 | Baird ........................................... 340/1 |
| 4,285,241 | 8/1981 | Smith et al. ............................... 73/579 |
| 4,824,016 | 4/1989 | Cody et al. .......................... 73/861.18 |
| 4,877,488 | 10/1989 | Cody et al. ............................... 73/579 |
| 4,973,386 | 11/1990 | Callegari et al. ......................... 73/579 |
| 4,993,264 | 2/1991 | Cody et al. ............................... 73/579 |
| 5,022,266 | 6/1991 | Cody et al. ............................... 73/579 |
| 5,022,268 | 6/1991 | Wolf et al. ............................... 73/602 |

FOREIGN PATENT DOCUMENTS

| | | | |
|---|---|---|---|
| 0385789 | 9/1989 | European Pat. Off. ........... B01J 8/24 |
| 0554640 | 8/1993 | European Pat. Off. ........ F04D 29/66 |

*Primary Examiner*—Hezron Williams
*Assistant Examiner*—Thuy Vinh Tran
*Attorney, Agent, or Firm*—Ronald D. Hantman

[57] ABSTRACT

The present invention is a non-intrusive method to determine the flow state or voidage in an apparatus that interacts a gas phase with a liquid phase. The flow state or voidage is determined by relating them to wall vibrations.

6 Claims, 11 Drawing Sheets

METHOD FOR DETERMINING OPERATING STATUS OF LIQUID PHASE GAS-PHASE INTERACTION COLUMNS

BACKGROUND OF THE INVENTION

The present invention relates to the operation of processes involving the interaction of a gas phase with a liquid phase, e.g., gas-liquid contacting, such as in fractional distillation in columns containing contact trays, evaporation, aeration, and mixing by flow through orifices, and injection into bubble column reactors.

Distillation is a common process in the petrochemical industry to efficiently separate chemical compounds. It may be defined as the separation of the constituents of a liquid mixture by partial vaporization of the mixture, followed by separate recovery of the vapor and liquid residue. Distillation towers, such as pipestills, contain a vertical distribution of "trays". The fluid, from which the separation of the vapor is made, flows over the trays driven by gravity. The trays contain holes through which the released vapor can flow to be separated eventually into a vapor stream exiting at the top of the tower. In some trays the gas flows through the liquid in the tray through "bubble caps" or "float valves", rather than "holes".

In some petrochemical operations, involving the interaction between a gas and a liquid, trays are also used to separate the gas stream from the liquid stream. In other operations such as bubble column reactor, it is important to maximize the contact between a gas or vapor and a liquid. In all these examples, there is a delicate balance in flow and state variables such as temperatures, pressures and flow rates in order to achieve the desired operation. In some cases mechanical components such as spargers or trays can operate improperly. In all these cases a critical component of the process is a finely dispersed mixture of gas and liquid which we call a "bubbly medium".

In what follows, distillation shall serve as the preferred embodiment, but the current invention can relate to any operation where the unit contains a significant region where the desired operating state is that of a "bubbly medium" such as a bubble column.

Figure 1:
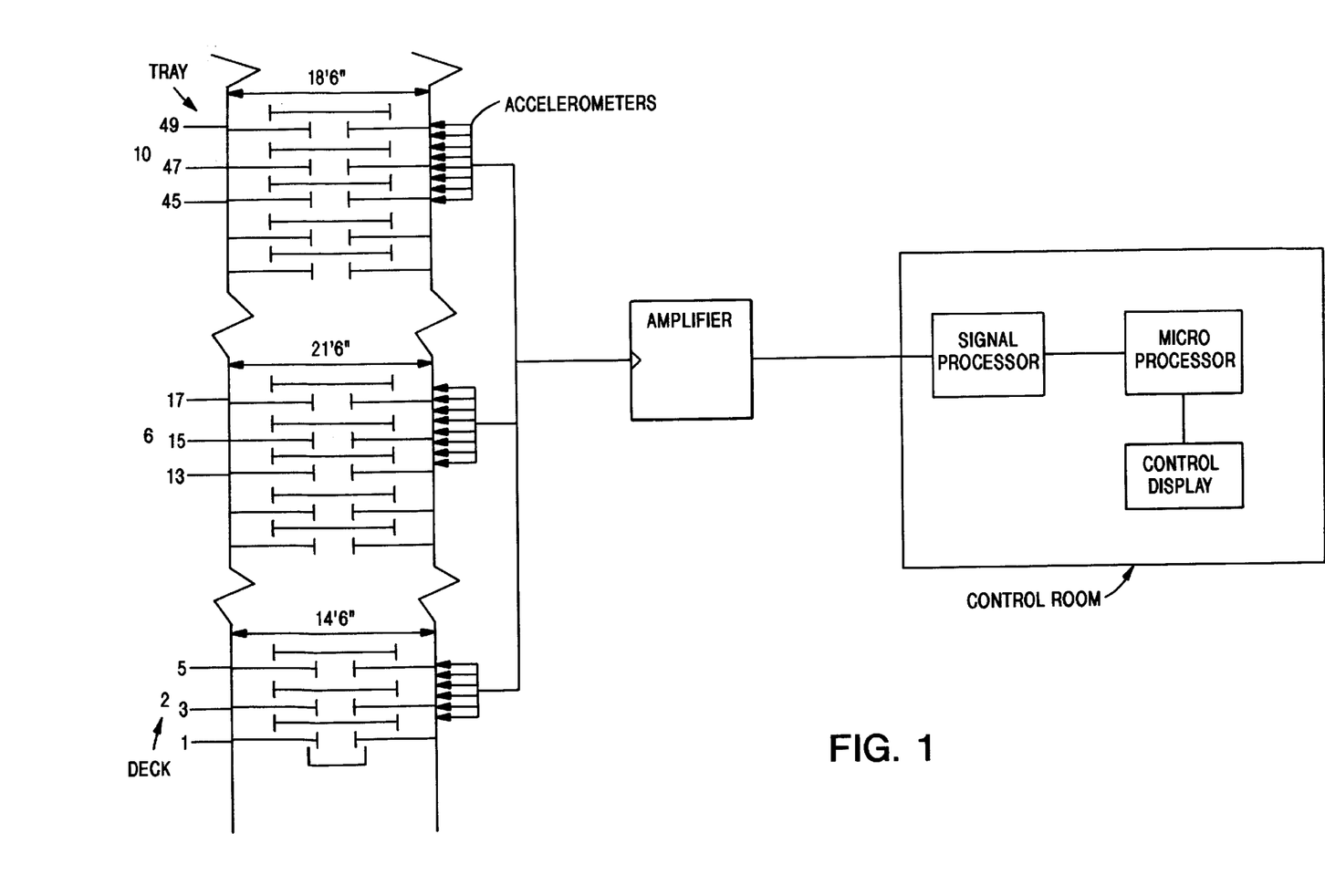
FIG. 1 shows a schematic showing the placement of accelerometers on the steel shell of a typical distillation tower and its coupling to the amplifier and signal processor.

In a pipestill, under ideal conditions, there is a clear separation of phases between what is flowing on the tray (a bubbly medium consisting of liquid plus rising vapor bubbles); what is flowing upward between trays (vapor or gas) and what is flowing downward through the "downcomers" (liquid). FIG. 1 is a schematic of a tower and shows the tray configuration. The trays are arranged in decks. FIG. 1 shows three decks with a number of trays within each deck.

Figure 2A:
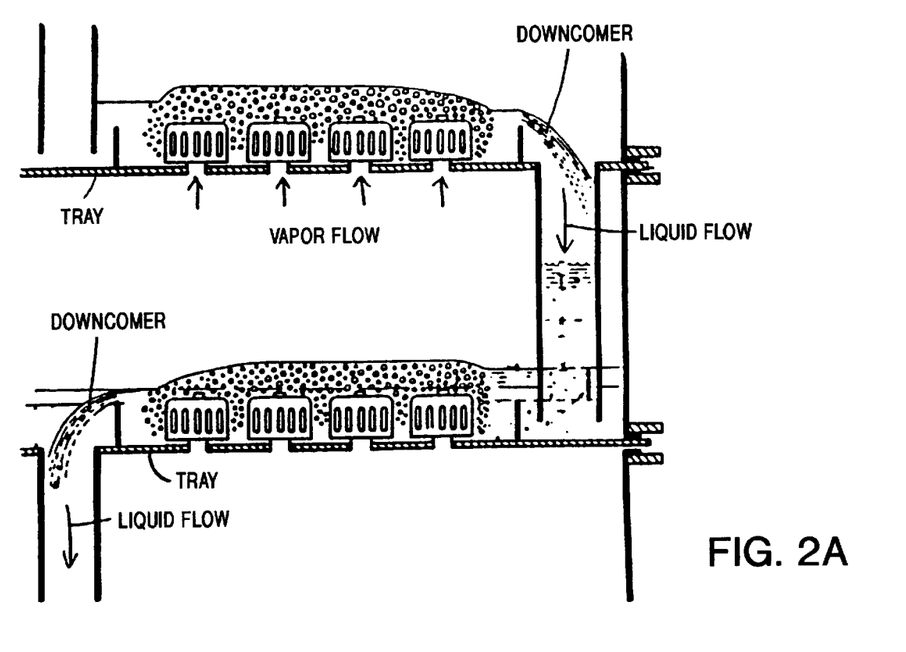
FIG. 2A shows a normal flow state.
Figure 2B:
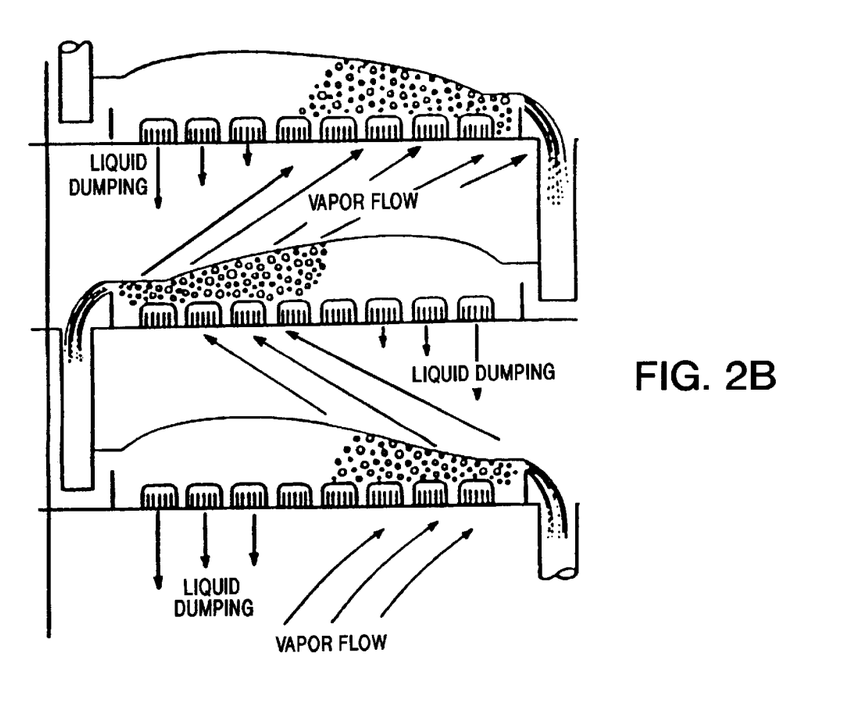
FIG. 2B shows an unstable flow state.

Maintaining such a desired flow state is difficult since it involves setting pressures differences at each tray such that vapor or gas is flowing upward through the holes in the tray and not liquid downward. Similarly, at the "downcomers" it is important that the liquid flows "down", and that the gas or vapor does not flow "up". Another problem that could occur is the generation of "foam", i.e. a froth of bubbles that leads to flow disturbance. In addition, the liquid level on the trays could be higher or lower than optimal due to improper design, excessive feed rates, or poor vapor/liquid separation. FIG. 2 shows a schematic of the flow state in a distillation column. FIG. 2A shows a normal flow state. FIG. 2B shows an unstable flow state.

In addition to the problem of setting the correct pressure differences to sustain the desired flow conditions in a tower that could be 100 feet high containing 50 or more trays, mechanical malfunctions could occur in the course of the operation. The holes in trays can become blocked through fouling. Trays can be physically displaced due to pressure surges and fall on top of other trays, and where the holes in the trays contain moving parts such as bubble caps, these parts can get stuck.

Malfunctions in the performance of distillation or fractionation are very difficult to identify directly from flow variables such as pressure or temperature. The loss of efficiency in the separation process can be expensive over the long run. Moreover, it is difficult to detect the area of repair from the variables that control the operation of the unit.

It would greatly assist in the operation of a distillation unit or any other processing unit that depended on its operation on an optimized "bubbly medium" if there was a technology that could monitor the operating state of the unit at each tray and alert operators to changes in that state from the ideal spatial separation of phases described above. It would be particularly advantageous if the technique was "non-intrusive" and thus did not require any penetration of the walls of vessel, and would not interfere with any of the operations of the unit. Finally, if the monitoring were continuous, the time between the suspicion of a malfunction and its identification could be reduced to a minimum, with considerable economic advantages. Corrective actions could then be taken, and their success (or failure) monitored. In some cases the unit might have to be removed from service to remedy the problem for example, "fouled trays' in the case of a distillation unit or a plugged sparger in a bubble column, but the repair could be scheduled with minimum lost time. However, it is important to note that portable monitors would also be useful where continuous monitoring is not justified.

Currently, information about the location and status of the internals of a distillation tower and liquid levels while the tower is operating can be supplied by gamma ray techniques. With these techniques a source of gamma rays is moved vertically down or up the tower, and a detector on the opposite side produces a signal that is proportional to the "density" of the material in the path of the beam. It is thus relatively easy to determine if the trays are in the right locations and liquid levels can also be determined. This technique is in common use in refineries and chem plants, but has serious drawbacks. First it is time consuming, not only in the time spent in making the survey, but in the time spent in scheduling the "scan", since it is supplied by outside specialized and licensed personnel. It is expensive; costing thousands of dollars. It is thus common practice to use this technique only when there are strong suspicions that a distillation or fractionation tower is not functioning as expected.

A more subtle weakness of the "gamma scan" technique is that it is only brought into play when there is evidence for a change in tower performance. Thus tower malfunctions that occur during start-up conditions can be overlooked as part of "normal operations".

Finally, there are processing operations which involve chemicals or pressures that require thick walls on the vessel. Under such conditions, or where the vessel containing the process is of a very large diameter, gamma scans lack the sensitivity to detect flow malfunctions within the unit.

There is thus a need for a less intrusive process than the "gamma scan" to monitor the flow state of a fractionation or distillation tower than can be applied and interpreted by refinery personnel. It is unlikely that it will be necessary to supply such the information in real time by a continuous link to a refinery control room. What is important, is the ability to know on demand, how a given unit differs from its past performance and from that of other similar units in other refineries. However, the invention described here can easily function in either mode. Gamma scans, as noted, can only supply information in a "batch" mode.

In the present invention, the magnitude of the signal from an accelerometer attached to the external wall of an atmospheric pipestill or a bubble column or any turbulently flowing liquid containing gas bubbles is used as a sensitive indicator of the flow state of the unit.

SUMMARY OF THE INVENTION

The present invention is a non-intrusive process where through accelerometers attached to the shell of a pipestill or other fractionation, separation system, or on the shell of a bubble column processing unit, one can determine the operating state of the system by a comparison made between current measurements and those made when the system was operating normally.

The method includes the steps of measuring wall vibrations of the structure and then determining the power spectrum as a function of frequency, the wall vibration measurements being taken at several positions along the structure wall in the vertical direction; determining the area of the power spectrum which includes a resonance peak for each of the positions; and correlating a change in the area of the power spectrum in the vertical direction with the flow state by comparing the power spectrum to the power spectrum of the position when the structure was operating efficiently.

BRIEF DESCRIPTION OF THE DRAWINGS

FIG. 2 shows the schematic of the flow state in a distillation column.

DESCRIPTION OF PREFERRED EMBODIMENT

The present invention is a passive acoustic process to monitor the flow state in a distillation tower or pipestill. The process is intended to permit operation of the pipestill under conditions that increase product yield or increase thermal efficiency or maintain performance over an extended period of time.

In order to utilize the invention, accelerometers are attached to the wall of the pipestill. The accelerometers are placed vertically along the pipestill wall at several locations. FIG. 1 shows a schematic of a pipestill indicating the trays and the placement of accelerometers. The electrical signal from the accelerometers, proportional to the wall's normal acceleration, is converted to a voltage and transmitted either by cable, optical, or wireless link to a control room. In the control room by suitable electronics, the power spectrum is determined as indicated in FIG. 1. The area under a certain peak of the power spectrum is then determined and is related to the flow state of the pipestill.

FIG. 1 also shows a schematic diagram of how the measurement of wall acceleration is made. A magnetically (or otherwise) attached accelerometer (such as a B and K 4384) produces an electrical charge output proportional to the instantaneous acceleration of the wall. This charge is converted by a charge amplifier (such as a B and K 2635) to a voltage output which is again proportional to the normal acceleration of the wall. This voltage is processed by a signal processor (B and K 2032 or equivalent) to produce the power spectrum of the acceleration. The power spectrum of the acceleration of the wall exhibits a peak located at a frequency corresponding to the wall resonance. Both the frequency of this peak and its area can be determined by a suitable computer algorithm.

FIGS. 2A and 2B show the flow state for normal flow and unstable flow in the pipestill.

Comparing the two figures shows that in normal flow (FIG. 2A) the liquid flow follows the downcomers while in unstable flow (FIG. 2B) the liquid dumps through the vapor flow holes.

Figure 3A:
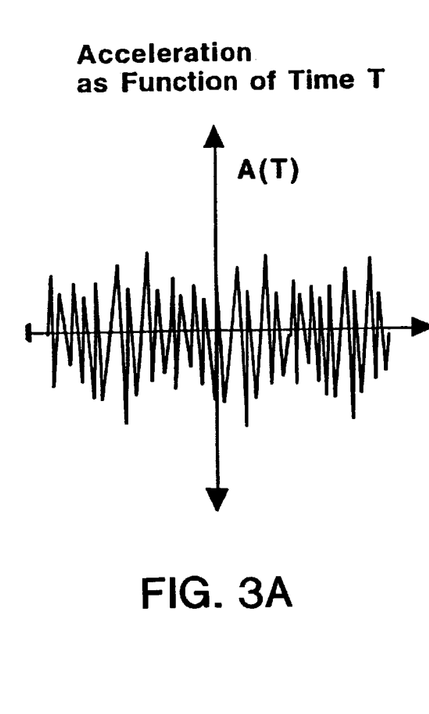
FIG. 3A shows a schematic of the signal produced by accelerometer as a function of time.
Figure 3B:
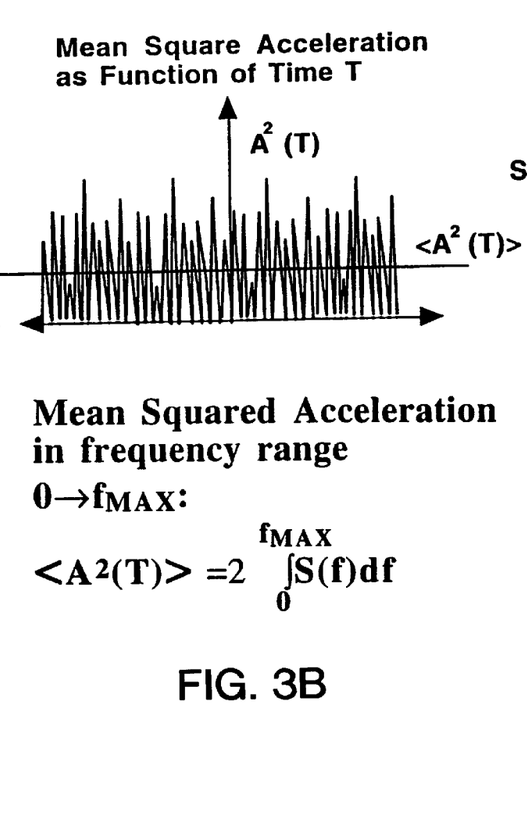
FIG. 3B shows the square of the signal produced by the accelerometer as a function of time and the relationship between the mean square acceleration and the area under the power spectrum.
Figure 3C:
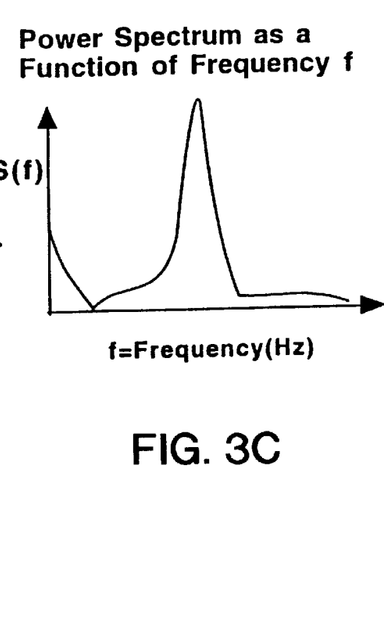
FIG. 3C shows the power spectrum as a function of frequency.

FIGS. 3A, 3B, and 3C exhibit the relationship between the time varying electrical signal produced by an accelerometer in contact with the distillation column and the frequency distribution of the vibrational energy generated by the nozzle in its operation. It also shows the square of that signal as a function of time and frequency and exhibits the well known relationship between the area under the power spectrum and the mean square signal (mean square acceleration or mean square pressure fluctuation when the transducers are correctly calibrated) produced by the vibrational sensor. There is a mathematical relation between the acceleration, A(T), which is random function of time, T, and the power spectrum of the acceleration, S(f), which is a function of frequency (f), such that the mean square acceleration, $<A^2(T)>$ over the frequency range $0-f_{max}$ is given by $$\langle A^2(T) \rangle = 2 \int_0^{f_{max}} S(f) df.$$

The RMS acceleration is the square root of the mean square acceleration, $<A^2(T)>$ The Power Spectrum may be related to Operating Conditions of the pipestill. The changes in operating conditions of the pipestill before turn-around, D1, (end of a run of operation) and just after turn-around, D2, (start of a run of operation) as summarized in the following Table 1.

Similarly, the area of the resonance peak ΔTOTAL also a dramatic change. For the trays in the vicinity of the 10th deck there is little change which suggests always marginal operation. Table 2 summarizes this data.

TABLE 2

PIPE STILL DATA

| Location | Date | D1 Total Amplitude M/s² (RMS 0–12.8 kHz) | D1 Resonant Peak M/S² | D1 Center Frequency HZ | D1 Peak Width HZ | D2 Total Amplitude M/s² (RMS 0–12.8kHz) | D2 Resonant Peak M/S² | D2 Center Frequency HZ | D2 Peak Width HZ |
|---|---|---|---|---|---|---|---|---|---|
| 2H | (514) | | | | | | | | |
| 2G | (4) | | | | | 32.9 | 32.3 | 5040 | 2496 |
| 2F | (4/3) | 0.17 | 0.125 | 5744 | 2096 | 35.8 | 32.3 | 7200 | 2496 |
| 2G | (3) | 0.161 | 0.139 | 5984 | 1808 | 29.2 | 25 | 6064 | 2064 |
| 2D | (3/2) | 0.159 | 0.092 | 5616 | 1360 | 45 | 44 | 5168 | 2064 |
| 2C | (2) | 0.179 | 0.149 | 5520 | 1888 | 41.4 | 40.8 | 4784 | 2736 |
| 2B | (2/1) | | | | | 52.6 | 51.3 | 4784 | 3136 |
| 2A | (1) | | | | | | | | |
| Average | | 0.17 | 0.13 | 5716 | 1788 | 39.48 | 37.62 | 5507 | 2499 |
| 6H | (17) | | | | | 2.87 | 2.2 | 5824 | 784 |
| 6G | (17/16) | | | | | 4.53 | 4.28 | 4960 | 1264 |
| 6F | (16) | | | | | 2.2 | 1.3 | 6576 | 832 |
| 6E | (16/15) | | | | | 3.53 | 3.15 | 5648 | 912 |
| 6D | (15) | 0.258 | 0.24 | 5280 | 1904 | 3.82 | 3.39 | 5648 | 912 |
| 6C | (15/14) | 0.275 | 0.25 | 6416 | 2992 | 3.24 | 2.38 | 6896 | 1648 |
| 6B | (14) | 0.201 | 0.14 | 7552 | 2240 | 2.75 | 2.28 | 7360 | 2209 |
| 6A | (14/13) | | | | | 4.25 | 3.72 | 5888 | 1888 |
| Average | | 0.24 | 0.21 | 6416 | 2379 | 3.40 | 2.84 | 6100 | 1306 |
| 10H | (49/48) | | | | | 0.158 | 0.0794 | 5888 | 1888 |
| 10G | (48) | | | | | 0.126 | 0.087 | 7520 | 2080 |
| 10F | (48/47) | | | | | 0.156 | 0.0946 | 6752 | 1968 |
| 10E | (47) | | | | | 0.238 | 0.146 | 4992 | 1968 |
| 10D | (47/46) | | | | | 0.171 | 0.0839 | 6608 | 1968 |
| 10C | (46) | | | | | 0.152 | 0.112 | 6480 | 3312 |
| 10B | (46/45) | 0.181 | 0.1212 | 5296 | 1904 | 0.198 | 0.1386 | 5648 | 2416 |
| 10A | (45) | 0.15 | 0.0657 | 7648 | 1344 | 0.201 | 0.1335 | 6448 | 2000 |
| Average | | 0.17 | 0.09 | 6472 | 1624 | 0.18 | 0.11 | 6292 | 2200 |

TABLE 1

OPERATING CONDITIONS OF AN ATMOSPHERIC PIPESTILL

| DATE | Before Turn-Around, D-1 | After Turn-Around, D-2 |
|---|---|---|
| Flow (nominal) | 100 kB/DAY | 138 kB/DAY |
| Trays 45–49 (10th Deck) | Bypassed, no liquid/vapor only/trays plugged | Same marginal operation |
| Trays 13–17 (6th Deck) | Marginal Operation | Normal |
| Trays 1–5 (2nd Deck) | Flooded, no vapor/liquid only | Normal |

Figure 4:
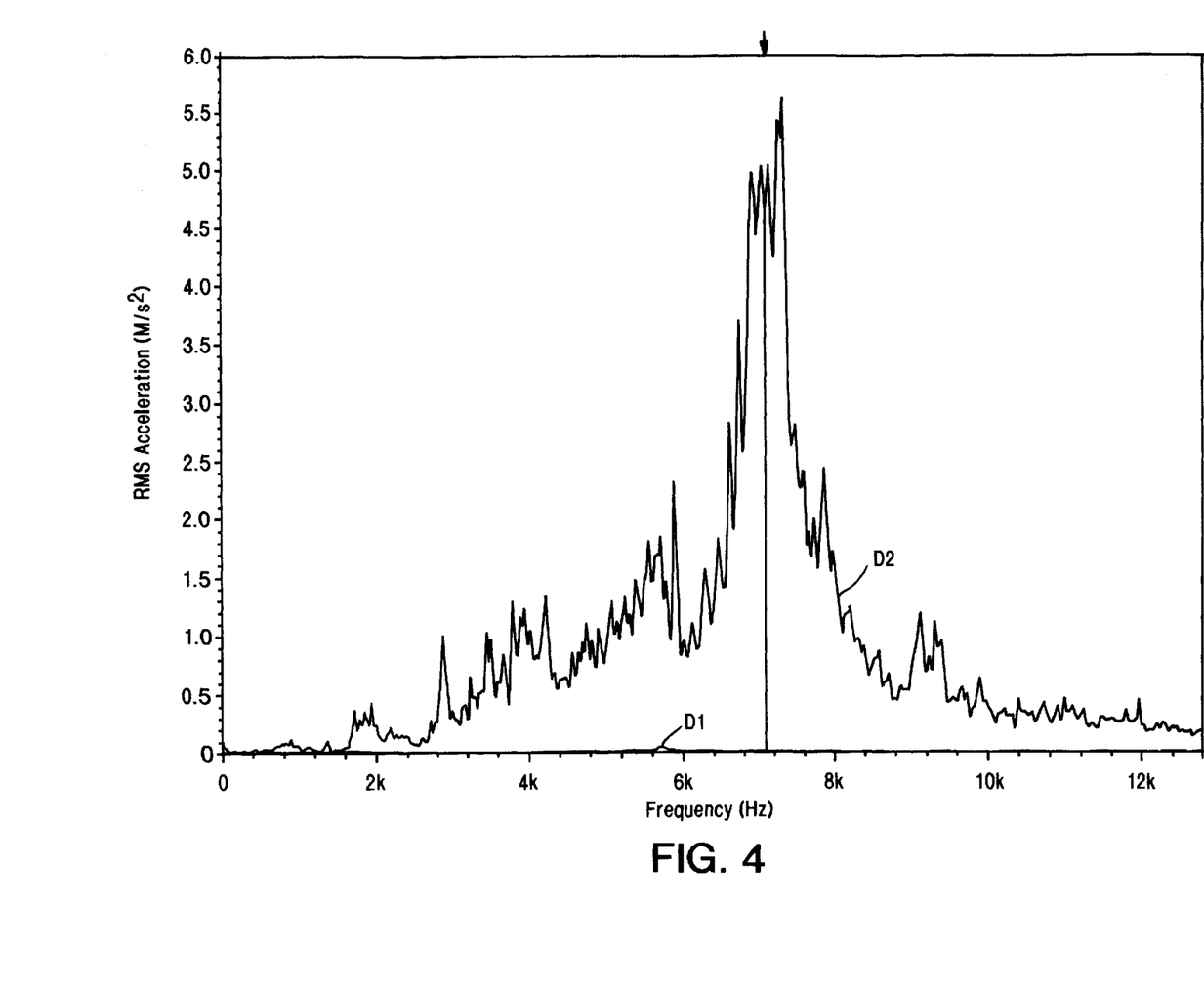
FIG. 4 shows the change in a typical power spectrum from the second deck of a distillation tower between measurement times D1 and D2 and illustrates the location of peak frequency and peak area.
Figure 5:
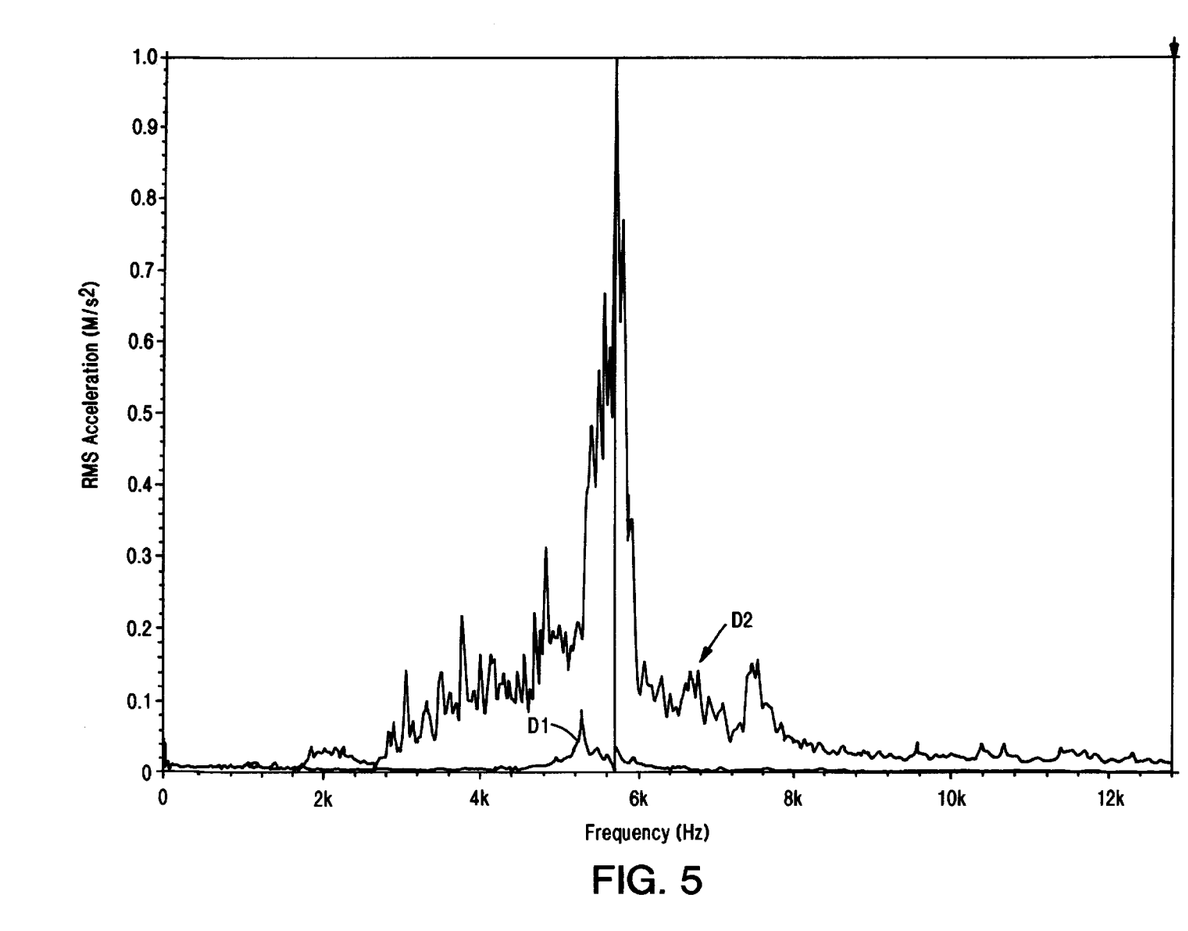
FIG. 5 shows the change in a typical power spectrum from the sixth deck of a distillation tower between measurement times D1 and D2 and illustrates the location of peak frequency and peak area.
Figure 6:
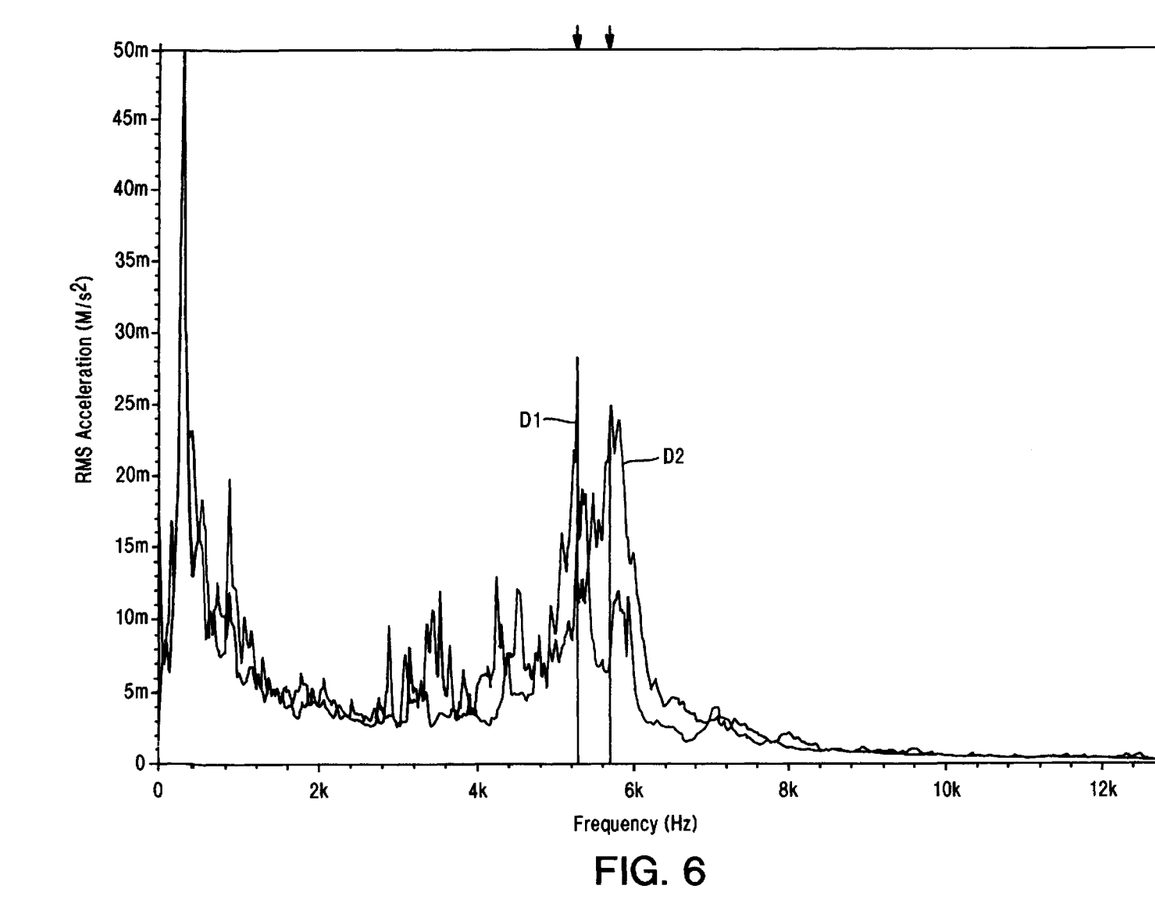
FIG. 6 shows the change in a typical power spectrum from the tenth deck of a distillation tower between measurement times D1 and D2 and illustrates the location of peak frequency and peak area.

FIGS. 4–5 exhibit the power spectrum obtained by analyzing the acceleration signal in a commercial signal processor (B&K 2032) at three specific locations. They are representative of all the data. The ordinate of each figure is the RMS acceleration in units of M/S² at each frequency. The abscissa is frequency over the range 0–12,800 HZ.

The dominant feature of the figures is a broad resonance centered at a frequency between ≈5000 Hz and ≈7000 Hz. As shown in Table 2, there is no significant change in the location of this peak between D1 and D2.

More significant is the dramatic change for trays in the vicinity of the 6th and 2nd deck in the area of the power spectrum or the TOTAL RMS acceleration over the frequency range 0–12,800 Hz (there is little power in the power spectrum above 12,800 Hz) between the two measurements.

The data in Tables 1 and 2 show that the RMS acceleration can be related to the flow state in a gas-liquid reaction column.

1. From Table 1, we see that the operating conditions for trays 1–5 on D1 were such that there was only liquid falling over the trays apart from steam injected into the tower. From Table 2 we note an enormous change (a factor of 230 in RMS magnitude or 5×104 in power [47 dB]) in the RMS acceleration, either in the resonance peak or over the range 0–12,800 Hz, between this date and D2. We are thus led to associate the change with the change to "proper tray operation" on D2, i.e. separated regions of vapor, liquid and vapor bubbles passing through the liquid and a well defined bubbly medium contiguous with the main sources of flow noise.

2. From Table 1, we see that the operating conditions for trays 13–17 on D1 were such that there was normal but marginal operations (compare the two states of a tray in the schematic of FIG. 2). From Table 2 we note a significant change (a factor of 14 in RMS magnitude or 228 in power [23dB]) in the RMS acceleration, either in the resonance peak or over the range 0–12,800 Hz, between this date and Nov. 17, 1987. We are thus led to associate the change in magnitude with the transition from "marginal" to "normal" operations on D2 (compare the two states of a tray in the schematic of FIG. 2) i.e. a change to desired flow distribution to an undesired flow distribution as shown in the figure.

3. From Table 1, we see that the operating conditions for trays 45–49 on D1 were such that there was no liquid present, but only vapor. From Table 2 we note a no change in the RMS acceleration, either in the resonance peak or over the range 0–12,800 Hz, between this date and D2. We are thus led to suggest that in this region of the pipestill, the flow state can be described as "marginal", by comparison with the magnitude of the RMS accelerations obtained in this region (trays 45–49) of the pipestill on D2, and the magnitude of the RMS acceleration obtained on D1 in the vicinity of trays 13–17. This hypothesis agrees with the observation that the trays in this region consistently "plug" in the course of the operations of the unit. At this stage this hypothesis can only be verified by a gamma scan in this region.

4. Consistent with the hypothesis that the change of signal is associated with changes in the spatial separation of liquid, vapor and bubbly phases is the fact that the total flow through the unit only changes by about 30% between D1 and D2 (100,000 b/D to 130,000 b/D).

Figure 7:
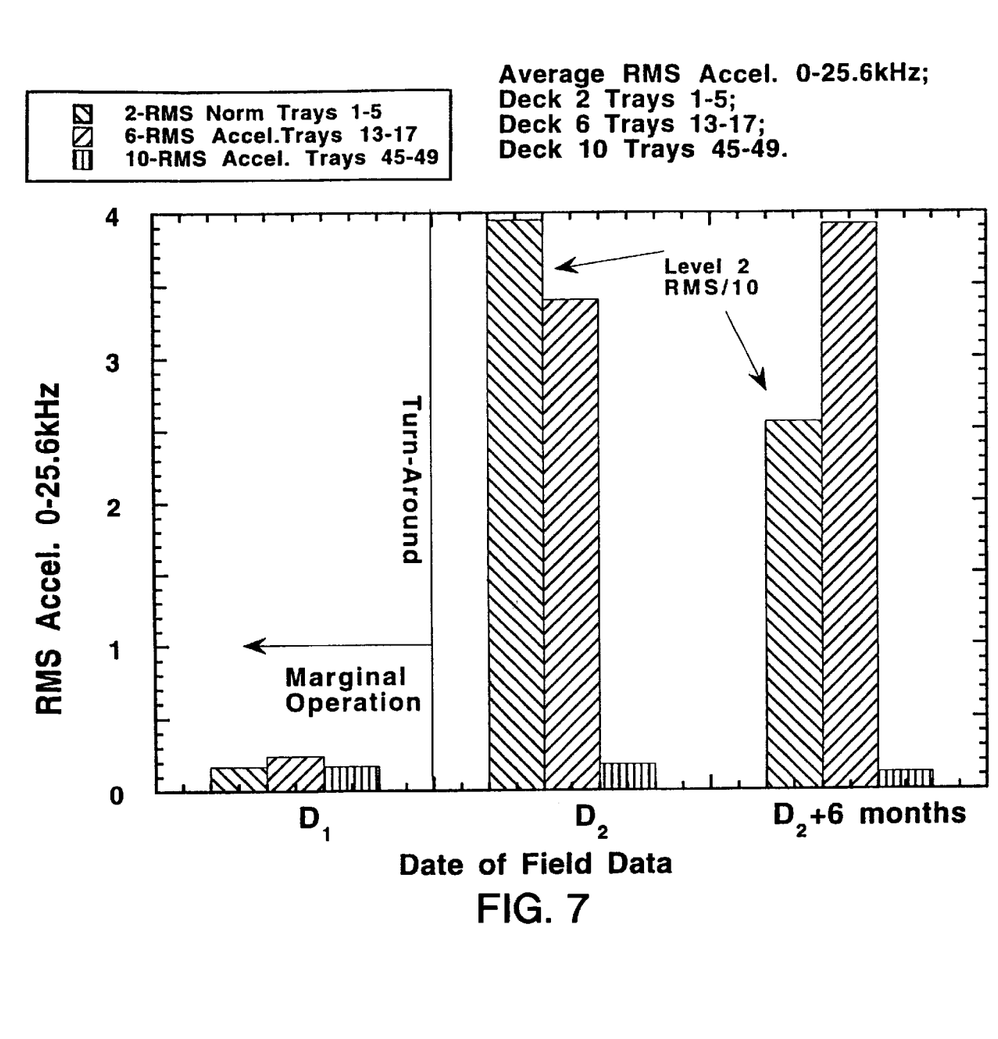
FIG. 7 shows a bar column figure comparison of the RMS acceleration between measurement times D1, D2 and D2 plus 6 months.

5. The fact that the amplitudes of the signals in the vicinity of trays 1–5 is about 10× that of the amplitude of the signals in the vicinity of trays 13–17 can be accounted for if we associate more vapor (steam or hydrocarbon?) flowing through the lower trays. FIG. 7 shows a bar column figure comparison of the RMS acceleration at D1, D2 and D2 plus 6 months.

It is surprising that a simple non-intrusive measurement made on the steel shell of the pipe still is capable of giving information that is location and operation specific. There are however a variety of physical mechanisms that could account for the data. The resonance peak itself is apparently flow related, since as shown in Table 2 it is present under all conditions at all levels. It is not associated with the diameter of the tower since as noted in FIG. 1, the diameter increases by 50% between the 2nd deck and the 6th deck, but there is no significant change in the average frequency of the resonance. The resonance might be related to turbulent flow through the outboard and inboard downcomers. We can derive from the average frequencies given in Table 2 a characteristics length from the usual acoustic formula:

$$f\lambda = c \tag{1}$$

In Eq. (1), the quantity "$f$" is the frequency of the sound, "$\lambda$" is the wavelength of the sound and the quantity "$c$" is the velocity of sound in the medium. It is common practice in acoustics to identify the source of a resonance, or concentration of energy in a peak in the power spectrum with a structural element that is of the same order or somewhat larger than the wavelength.

If we note that the velocity of sound in hydrocarbons is about 1000 M/sec., we can deduce a wavelength of the order of 6 inches for a resonant frequency of 6400 Hz. This length is of the same order but smaller than the characteristic dimensions of the downcomers. In the pipestill under consideration, tray separation at the 2nd deck location is 27", at the 6th deck location 24", and at the 10th deck location 27".

If we note that the velocity of sound in the gas phase is about 500 M/sec., the wavelength is about three times the diameter of the holes in the trays.

On the other hand, it is well known from the acoustic literature that turbulent flow produces characteristic resonances due to the process called "vortex shedding" (cf. Mechanics of Underwater Noise by Donald Ross, Pergamon Press (New York 1976, chapter 9). Again one can deduce a characteristic distance "L" which is given by the quotient of the Velocity of Flow, V, and the frequency of the resonance peak, F. In general $$L \approx V/F \tag{2}$$

For a flow velocity of 1 ft/sec (=V) we derive a characteristic length for F≈5000 Hz of L≈3 mils. Clearly to get magnitudes of L at least of the order of the smallest length of the problem (the thickness of the trays ≈⅛ inch) we need velocities at least of the order of ≈50 ft/sec. This appears to be somewhat larger than would be expected for flow over the weir of a tray, but is not out of line.

The vibrations in the power spectra in FIGS. 3–5 arise from turbulent flow due either to gas flow or liquid flow or due to acoustic resonances with the downcomers. The fact that there is no significant difference between the frequencies of the resonance in the 10th deck (trays 47–49) of the tower between the drastically different operating conditions of D1 (bypassed vapor only no liquid) and D2 (liquid and vapor) suggests that the resonance arises from vapor flow through the holes in the trays or through the turbulence in the liquid stream entering the tray from above.

It is easier to physically account for the dramatic changes in the vibrational acceleration between the two dates. One explanation to the greatly increased magnitude of the signal with the transition to proper operating conditions on D2 (for all but trays 45–49) might be the enhanced effectiveness of sound radiation to a vapor space by the "bubbly liquid" contained in the tray (see Ross, chapter 2 for a discussion of the poor coupling between sound in a liquid and a gaseous medium). Another explanation is the enhanced coupling between turbulent flow noise and sound due to the presence of bubbles in the flow (see e.g. Crighton and Ffowcs Williams, J. Fluid Mech 36 pp 585–603, (1968)). In both cases it is easy to account for increases in RMS amplitude of the order of 200 or so given in Table 2.

Figure 8:
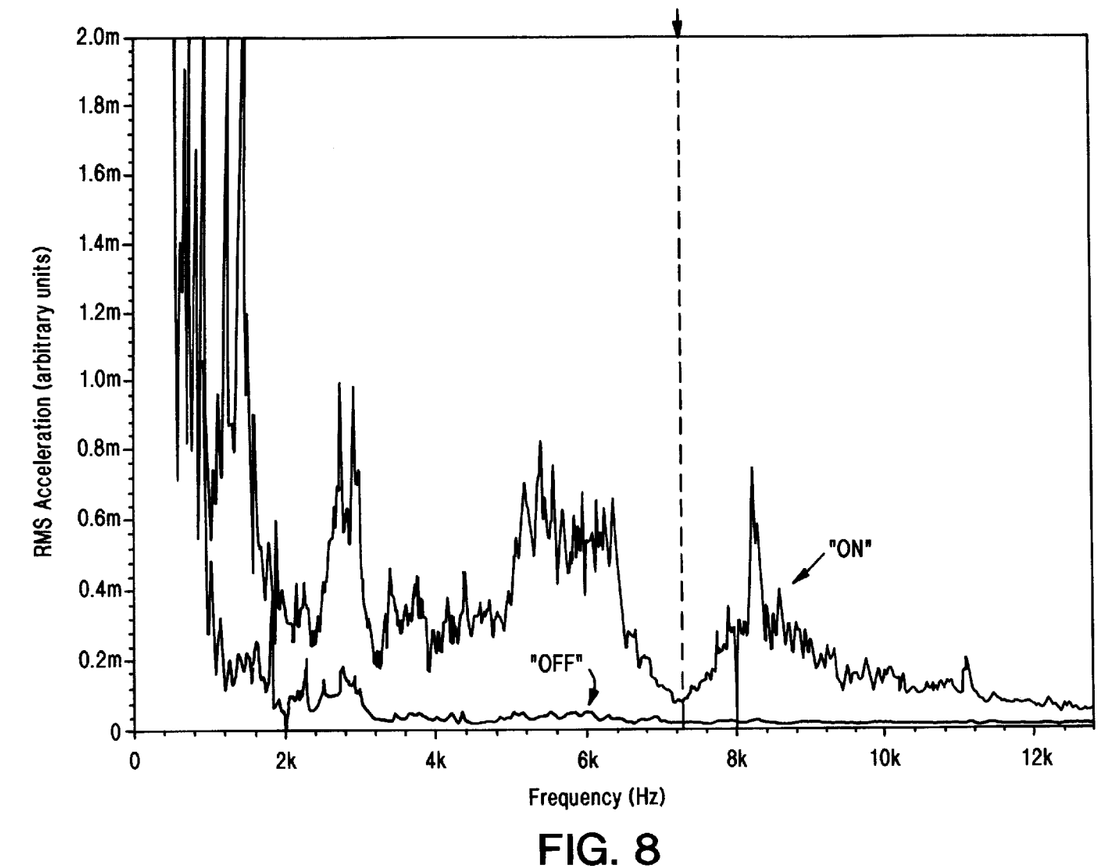
FIG. 8 shows the effect of a "bubbly" medium (propylene injection) on flow noise in the power spectrum of a pipe containing sulfuric acid.

Pilot plant studies on a bubble column support the view that dispersion of gas in a liquid can lead both to an enhancement of flow noise and to a reduction of flow noise. FIG. 8 shows the effect of a "bubbly" medium (propylene injection) on flow noise in the power spectrum of a pipe containing sulfuric acid.

The effect of adding air with a sparger to water flow on the flow noise power spectrum of a bubble column is summarized in Table 3. In all the cases the RMS pressure determined by a hydrophone is a band of 9088 Hz starting at 3232 Hz (i.e. just above the low frequency peak associated with pump noise) is the largest for "bubbly flow."

TABLE 3

| RMS PRESSURE AT A HYDROPHONE LABORATORY IN A BUBBLE COLUMN UNDER DIFFERENT FLOW CONDITIONS | | |
|---|---|---|
| Water (GPM) | Air (SCF) | RMS Pressure (3232–12.320 Hz) |
| 200 | 0 | 0.29 Pa |
| 200 | 50 | 0.65 Pa |
| 200 | 100 | 3.6 Pa |
| 0 | 100 | 1.47 Pa |

Table 3 shows the relationship between RMS pressure and air bubbles in a bubble column as measured by hydrophone.

Figure 9:
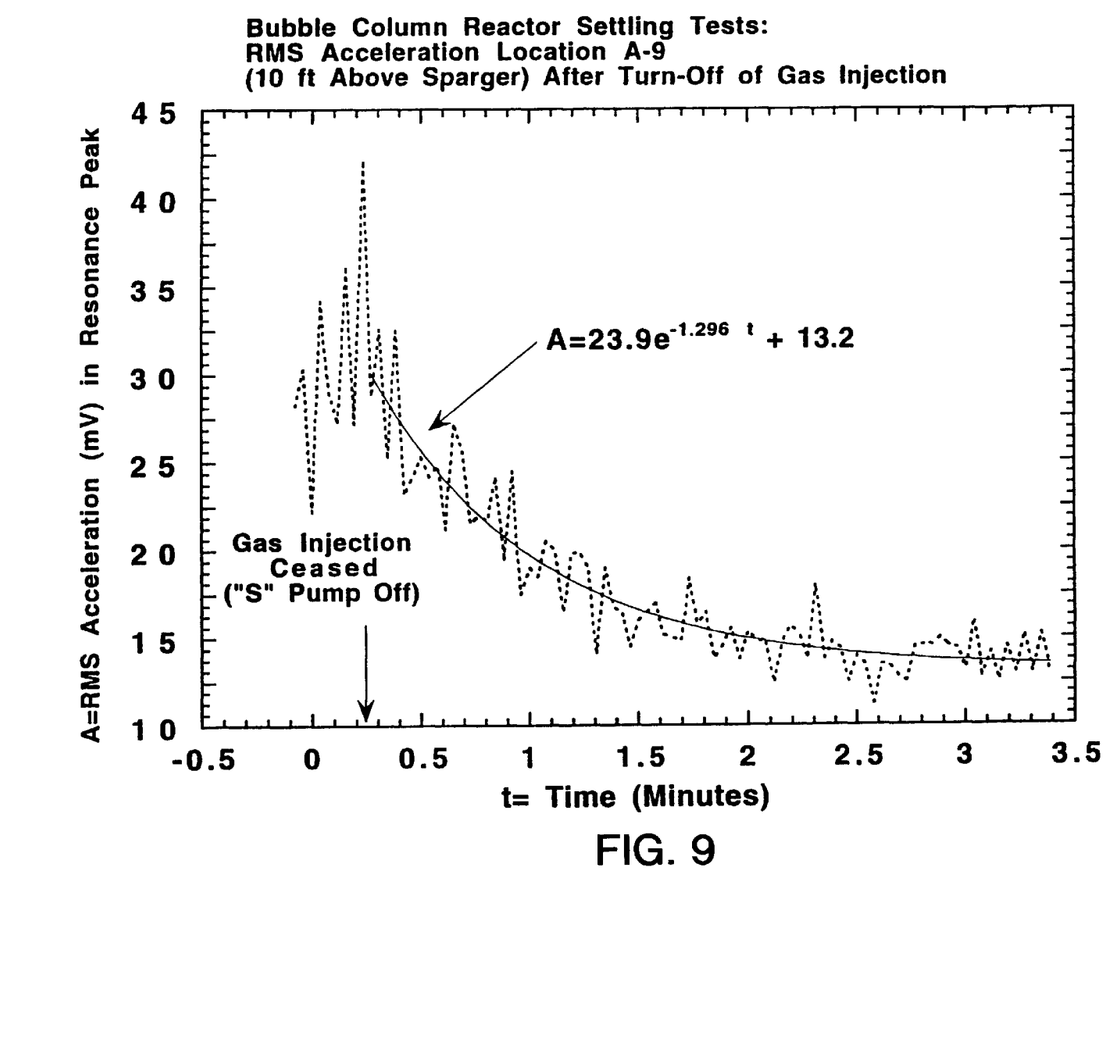
FIG. 9 shows the relationship between RMS acceleration and time in a bubble column when gas injection stops.
Figure 10:
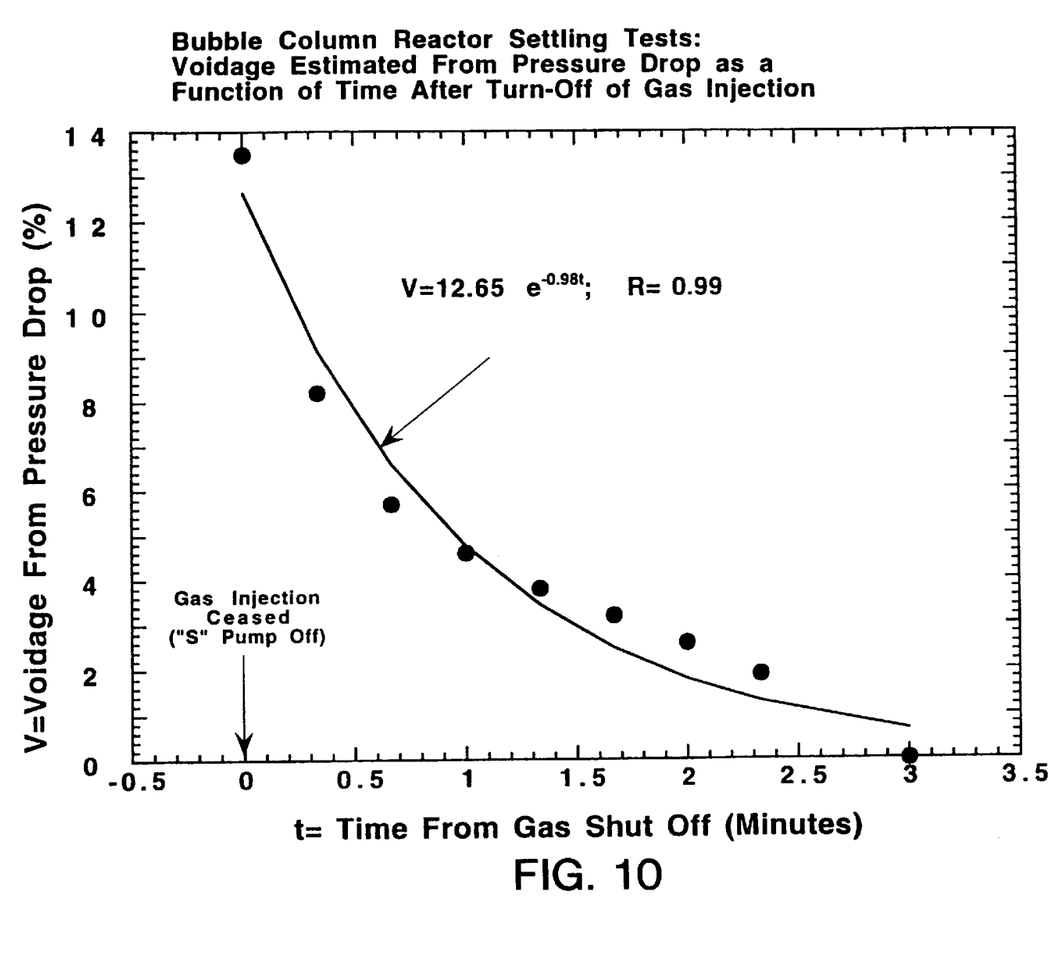
FIG. 10 shows the relationship between voidage and time in bubble column when gas injection stops.
Figure 11:
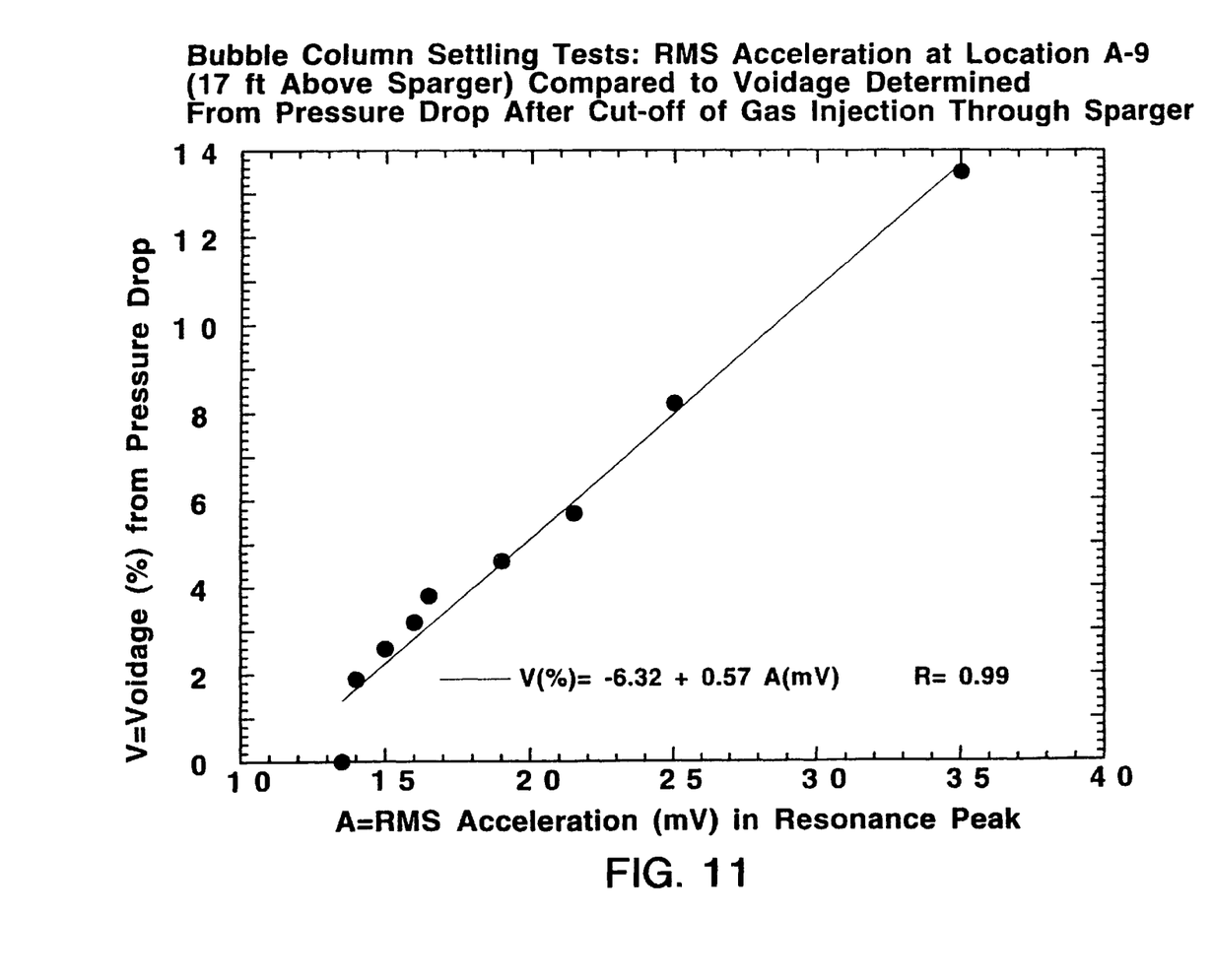
FIG. 11 shows the linear relationship between voidage and RMS acceleration in a bubble column when gas injection stops.

Air bubbles may be related to percent voidage in the bubble column and measured not by a hydrophone in liquid but by accelerometers on the wall of vessel. A sparger injected gas bubbles into a bubble column. The RMS acceleration was determined 10 ft. above the sparger after the gas injection ceased (see FIG. 9). The voidage was estimated from the pressure drop after the gas injection ceased (see FIG. 10). These results are combined to show a direct relationship between voidage and RMS acceleration (FIG. 11).

With these results, it is not surprising that the major vibrational effect of a return to normal operating conditions is the increase the amplitude of the vibrational signal measured external to the fluid by a measurement of the acceleration of the wall.

What is novel and surprising is that the effect can be observed so simply and non-intrusively by an accelerometer mounted on the shell of the unit. The data in Table 2 was obtained by magnetically attached accelerometers spaced at distances equal to one half the tray separation (27" apart at the 10th deck, 24" apart at the 6th deck and 27" apart at the 2nd deck). It is also surprising that the amplitude of the data shown in Table 2 varies with location.

Therefore, the present invention is a non-intrusive process where through accelerometers attached to the shell of a pipestill or other fractionation, separation system, or on the shell of a bubble column processing unit, one can determine the operating state of the system, by a comparison made between current measurements and those made when the system was operating normally.

One example of an application would be permanently attached accelerometers whose output is brought down to a junction box at the base of the unit. On a weekly basis the acceleration signal would be recorded and sent to a central location where the data from the present unit or other similar processing units whose power spectra were available in a data base. Departures from normal signal levels would be interpreted in the light of past experience and recommendations made to the operator on the condition of the unit.

In some cases, for example a plugged or damaged tray, this might suggest a gamma ray scan to verify precisely where the malfunction occurred. In other cases, changes might be made in operating conditions to see if conditions could be brought back to normal. In all cases there would be a considerable savings in operating energy costs for the unit as well as the elimination of unnecessary gamma scans. Given the inherently low cost of the vibrational technology and its non-intrusive nature installation of such a system would have a very high benefit/cost ratio.

What is claimed is:

1. A method for the non-intrusive determination of the flow state of a gas phase interacting with a liquid phase in a structure comprising:

(a) measuring wall vibrations of said structure and then determining the power spectrum as a function of frequency, said wall vibration measurements being taken at one or more positions along the structure wall in the vertical direction;

(b) determining the area of the power spectrum which includes a resonance peak for each of said positions;

(c) correlating a change in said area of the power spectrum in said vertical direction with said flow state by comparing the power spectrum to the power spectrum of the position when the structure was operating efficiently.

2. The method of claim 1 wherein said structure is a distillation tower.

3. The method of claim 1 wherein said structure is a pipestill.

4. The method of claim 1 wherein said step of measuring wall vibrations is performed by using an accelerometer.

5. The method of claim 1 wherein said power spectrum is between 4000 and 8000 Hz.

6. A method for the non-intrusive determination of the voidage in a bubble column comprising:

(a) measuring wall vibrations of said structure and then determining the power spectrum as a function of frequency, said wall vibration measurements being taken at several positions along the structure wall in the vertical direction;

(b) determining the area of the power spectrum which includes a resonance peak for each of said positions;

(c) correlating a change in said area of the power spectrum in said vertical direction with said flow state with said voidage in said bubble tower.

* * * * *